United States Patent [19]
Feldberg et al.

[11] Patent Number: 6,026,331
[45] Date of Patent: Feb. 15, 2000

[54] TREATMENT APPARATUS

[75] Inventors: Ian Feldberg; Nigel Cronin, both of Avon; Martyn Evans, Gwent; Nicholas Sharp; Suzanne Smith, both of Avon, all of United Kingdom

[73] Assignee: Microsulis Limited, United Kingdom

[21] Appl. No.: 08/569,179

[22] PCT Filed: Jul. 19, 1994

[86] PCT No.: PCT/GB94/01565

§ 371 Date: Apr. 29, 1996

§ 102(e) Date: Apr. 29, 1996

[87] PCT Pub. No.: WO95/04385

PCT Pub. Date: Feb. 9, 1995

[30] Foreign Application Priority Data

Jul. 27, 1993 [GB] United Kingdom ............ 9315473
Feb. 1, 1994 [GB] United Kingdom ............ 9401912

[51] Int. Cl.[7] .................................................. A61N 5/02
[52] U.S. Cl. ........................... 607/102; 606/33; 600/2
[58] Field of Search ........................... 600/2; 601/15; 606/14, 31, 33; 607/101, 102, 156; 128/504

[56] References Cited

U.S. PATENT DOCUMENTS

| 2,509,196 | 5/1950 | Cork . | |
|---|---|---|---|
| 4,378,806 | 4/1983 | Henley-Cohn | 128/504 |
| 4,776,086 | 10/1988 | Kasevich et al. | 607/101 |
| 4,800,899 | 1/1989 | Elliott | 607/102 |
| 5,026,959 | 6/1991 | Ito et al. | 607/101 |
| 5,344,441 | 9/1994 | Gronauer | 607/102 |
| 5,358,515 | 10/1994 | Hurter et al. | 607/101 |

FOREIGN PATENT DOCUMENTS 56-166605  12/1981  Japan .
60-180302  1/1985   Japan .

OTHER PUBLICATIONS

Navy Technical Disclosure Bulletin, vol. 14, No. 1 (Dec. 1988).

Primary Examiner—Mark S. Graham
Attorney, Agent, or Firm—Jones & Askew

[57] ABSTRACT

A probe (1) is designed to propagate and radiate microwave electromagnetic energy in a controlled fashion. The probe (1) includes at least one waveguide (2) of cross-section which would not normally pass microwaves at the operational frequency. The waveguide (2) therefore includes dielectric material (5), such as alumina, in the form of a rod an exposed portion of which forms an antenna. The probe is preferably for use in endometrial ablation and therefore the reduced dimension of the waveguide can be made compatible with the narrow neck of the uterus.

16 Claims, 7 Drawing Sheets

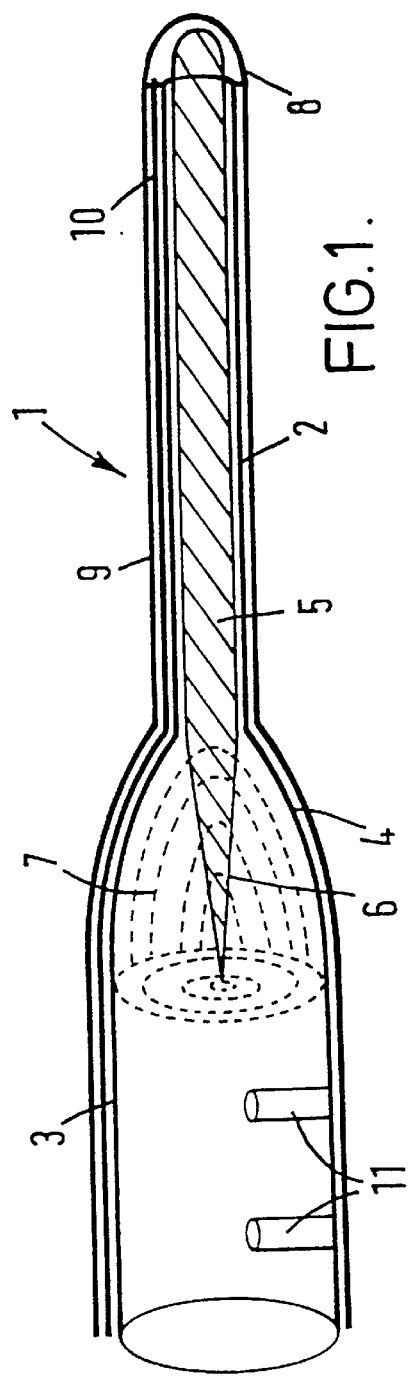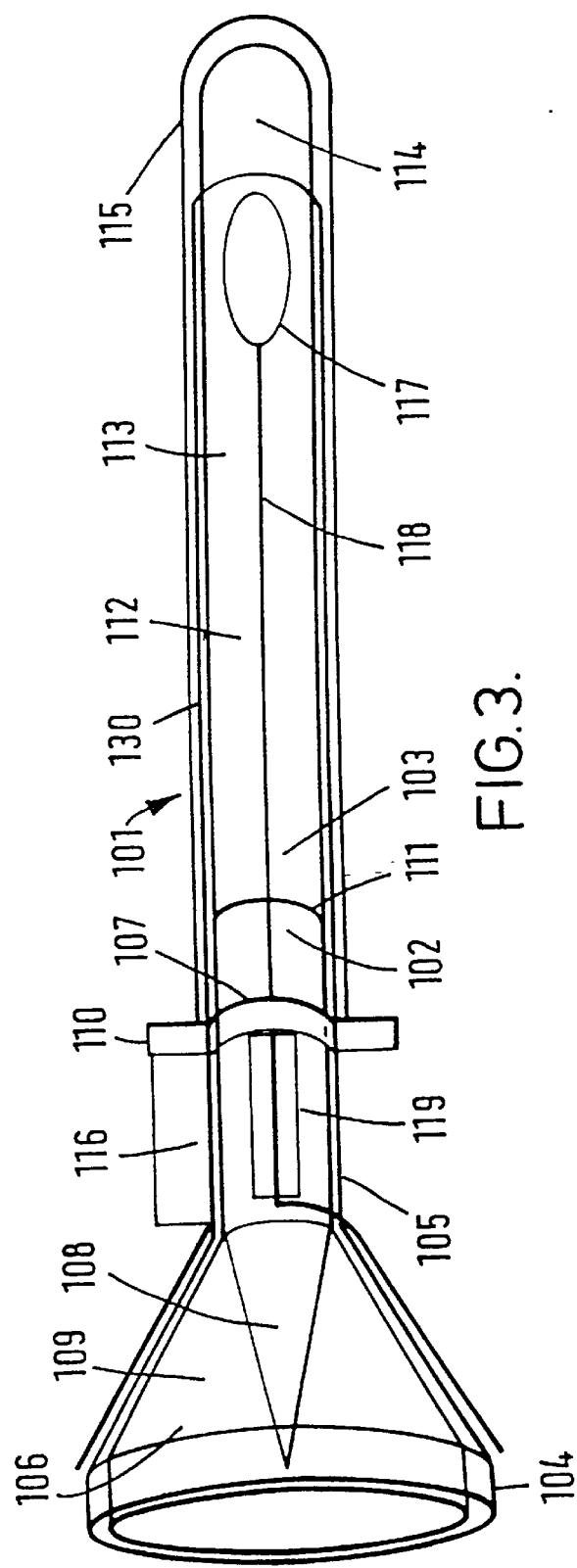

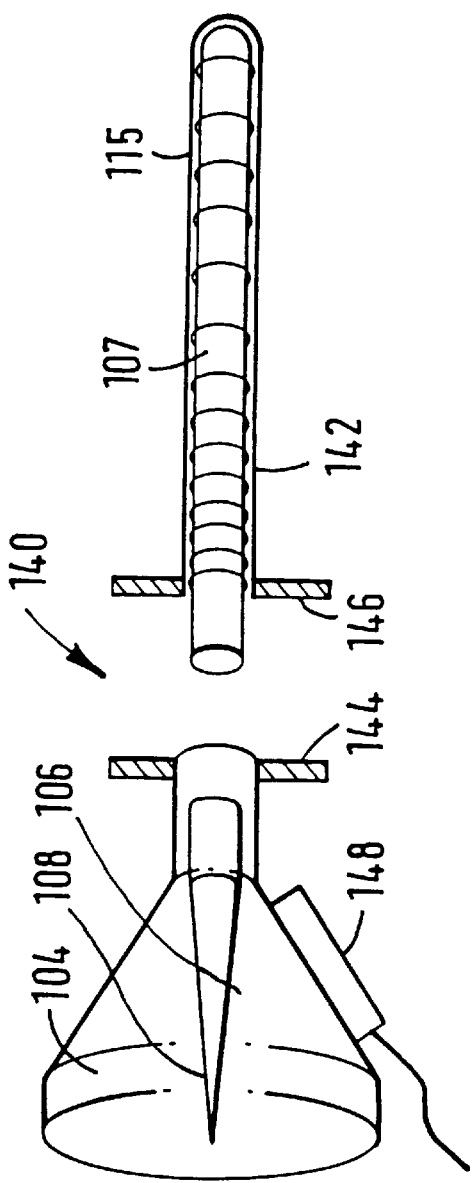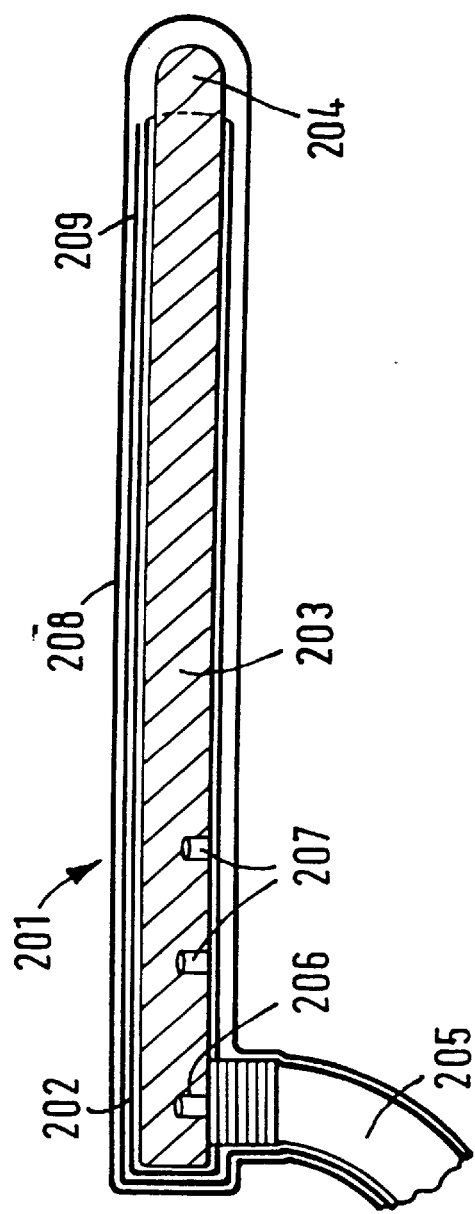

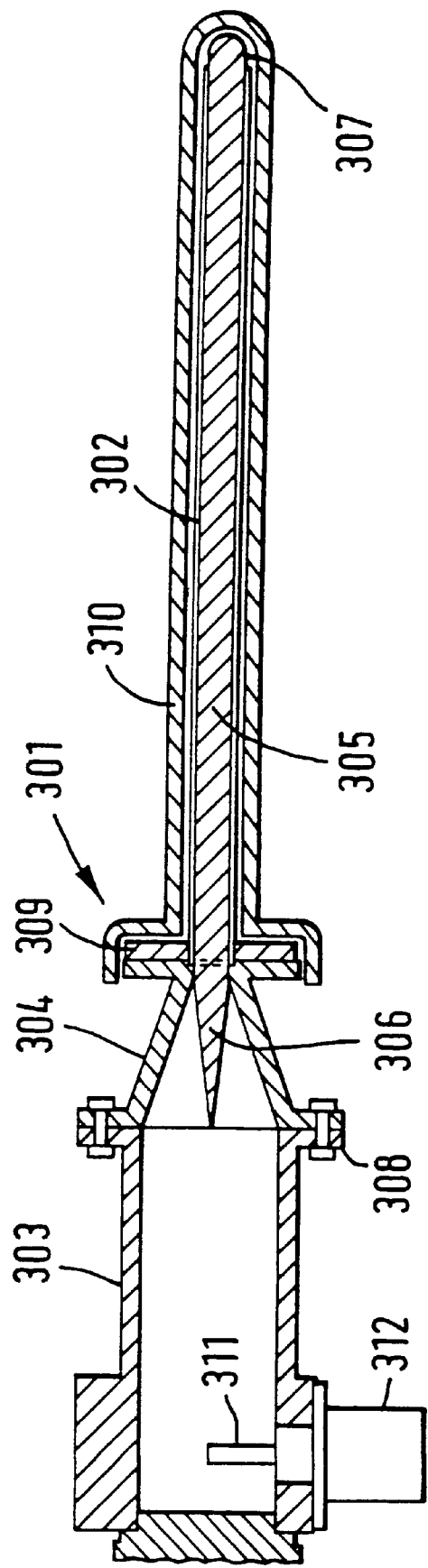

TREATMENT APPARATUS

FIELD OF THE INVENTION

This invention relates to apparatus for the treatment of a body by means of microwave electromagnetic energy. The body is preferably biological tissue and, in particular, it relates to apparatus for use in the treatment of menorrhagia. However, the apparatus may have other uses for the application of microwave electromagnetic energy to appropriate loads. The invention also includes a method of treatment using the apparatus.

DESCRIPTION OF THE PRIOR ART

Menorrhaaia is a common condition in women over the age of forty and manifests itself as excessive bleeding from the endometrium which constitutes the inner wall of the uterus. The result is exceptionally long and heavy periods which can be severely debilitating because the blood loss leads to iron deficiency anaemia in addition to the general distress and inconvenience which it causes. The most common form of treatment is to carry out a hysterectomy in which the entire uterus is removed. However, not only is major surgery expensive but the patient also has to endure the distress and long period of convalescence. It is for these reasons that alternative treatments have been sought. The lining of the uterus which is shed at each menstrual cycle develops from the endometrium which is about 5 millimeters thick and covers the whole of the inner wall of the uterus. Menorrhagia can be cured, or at least alleviated, if the endometrium is wholly or partially destroyed without surgery. This destruction can either be achieved by physical means or by heating the tissue or a combination of both. In common with most body tissue, a temperature of around 60° C. maintained in the endometrium for up to 5 minutes will destroy its cells. Because it will no longer be possible for the endometrium to regenerate the lining the condition will be cured.

The current known alternative techniques to hysterectomies work with varying degrees of success but all have disadvantages. The uterus is a very delicate V-shaped pouch-like structure and the opposite walls are normally separated by a thin film of fluid or may be partly in contact. Therefore it is difficult to gain access to the endometrium for the purpose of direct physical treatment or for heating it. It is particularly difficult to treat the tissue immediately surrounding the entrance as heating must be confined to the endometrium itself and not extend to the main body of the uterus and beyond it.

The easiest and least complicated alternative method uses a steel ball about 5 mm in diameter heated by a monopolar connection to a power supple. The ball is rolled around in the uterus under the control of the surgeon to destroy the endometrium. However, the method is time consuming and requires highly specialised surgical experience. Even in skilled hands localised burning can occur or other areas are not fully treated.

It is also known to use certain forms of electromagnetic energy, for example, cell destruction has been achieved by laser ablation where light waves are used. However, laser treatment requires expensive laser equipment and the treatment has to be carried out using highly specialised surgical skills.

From European Patent Publication 0407057 it is known to use radio frequency electromagnetic energy. For example, the method disclosed in that patent involves placing a radio frequency probe in the uterus and setting up a radio frequency field between it and a steel belt around the patients waist. The treatment takes up to 45 minutes including anaesthetic induction and recovery. The procedure itself takes about 15–20 minutes and requires the full time attention of a skilled gynaecologist in moving the probe. This is because, as the typical power used is about 550 watts and radio frequency electromagnetic radiation is difficult to contain it has to be moved close to the endometrium to be at all effective. It also has the disadvantage that radio frequency electromagnetic energy readily passes through most materials (including tissue) and may very easily leak and insidiously cause injury to both the patient and surgical staff during the course of treatment.

Another method using radio frequency energy is disclosed in European Patent Publication No. 0115420 which discloses a device for hyperthermia therapy using first and second electrodes at al frequency of about 3–30 MHZ.

SUMMARY OF THE INVENTION

An object of the present invention is to provide an improved apparatus and method using microwave frequency electromagnetic radiation.

Microwaves at about 2.7 GHz are commonly used for cooking because of the strong absorption of radiation at that frequency by water. It therefore might be thought that given the use of light frequency and radio frequency electromagnetic radiation it would be obvious to try microwaves. However, there are no particular restrictions on waveguide or cavity size with microwave ovens therefore a frequency as low as 2.7 GHz and a wavelength of 100 cm or more presents no problem.

However, the neck of the uterus can only be dilated to about 10 mm diameter at maximum and any probe therefore needs to have a diameter of no more than 8 mm for general use. With conventional design this would mean that the microwave frequency would need to be much too high using conventional waveguide of these dimensions and not enough power would be delivered to the endometrium i.e. the higher the frequency the less the depth of absorption by the tissue being treated. It was also thought that standing wave patterns would produce non-uniform heating. However, standing waves only occur where there are reflections present and we have found that the walls of the uterus rather than causing are reflections absorb the waves by the lossy tissue of the endometrium which rapidly reduces the wave to zero before it can reach any potential reflecting objects.

According to the present invention there is provided a probe for applying electromagnetic radiation at microwave frequency to a body comprising means for receiving microwave signal input of a predetermined frequency, a waveguide for receiving and propagating said microwave frequency input, said waveguide being of a cross-sectional dimension which would not normally pass the microwaves at said frequency, dielectric material within the waveguide, the dielectric constant of which varies the cut-off frequency of the waveguide so that it may propagate desired modes of the microwaves at said predetermined frequency, and an exposed antenna portion at or adjacent an end of the probe allowing wave transmission away from the probe.

The means for receiving the microwave signal may comprise a second waveguide, transition means being provided between the first and second waveguides. In this arrangement the first waveguide is suitably a circular waveguide typically of about 10 mm diameter. The second waveguide may also be a circular waveguide of about 20 mm diameter. The transition means comprises a tapered waveguide interconnecting the first and second waveguides and loaded with dielectric material.

The dielectric material is preferably in the form of a ceramic rod having a tapered end at the transition to optimise transition and extending outwardly beyond the first waveguide to form the exposed antenna portion of the probe. The use of a dielectric filled first waveguide in accordance with the invention allows the first waveguide to be of smaller diameter because, at a given frequency, the wavelength in dielectric is shorter. Hence, the diameter of the probe in wavelengths remains constant throughout transition. For any given wavelength the minimum diameter of the probe is around one half of a wavelength. Any smaller and the wave will not pass through. The tapered end of the ceramic rod overcomes the dielectric mismatch between air In the second waveguide and the ceramic material. Without the taper there would be a danger of a reflection at the interface between the first and second waveguides.

In an alternative arrangement a single waveguide is provided and the means for receiving the microwave input directly excites the dielectric filled waveguide of the desired smaller cross-sectional dimension.

The preferred form of probe includes temperature sensors disposed between the first waveguide and a protective sheath. The sensors may be of different lengths in order to detect temperatures at different locations along the length of the probe and are united at a temperature sensor interface.

Although it is preferred that the probe be a single unit it is possible for the probe to comprise two or more separable portions. Therefore, according to another aspect of the invention a probe for applying electromagnetic radiation at microwave frequency to a body has a first dielectric stage and a second dielectric stage, the two stages, in use, being operatively connected together the firs. dielectric stage comprising a first waveguide of a first cross-section; a second waveguide of a second cross-section larger than the cross-section so the first waveguide for receiving and propagating microwave signal input of a predetermined frequency, and transition means between the first and second waveguides including dielectric material, the dielectric constant of which varies the cut-off frequency of the first waveguide so that it may propagate said microwave signal at the predetermined frequency; and, the second dielectric stage comprising a probe antenna of dielectric material, a third waveguide about a portion of the dielectric material and being of substantially the same cross-section as the first waveguide, and an exposed antenna portion at or adjacent a free end of the probe allowing wave transmission away front the probe.

Preferably, the transition means of the first. dielectric stage comprises a tapered waveguide interconnecting the first and second waveguides, a tapered end on the dielectric material within the tapered waveguide to optimize transition and a dielectric buffer between the tapered end of dielectric material and the tapered waveguide, the dielectric constant of which is greater than air but less than that of the dielectric material.

In this arrangement the probe may be for endometrial ablation and the second dielectric stage may include opposed inflatable catheters to aid positioning in the uterus. Suitably, the second dielectric stage also includes temperature sensing means. Where provided with two stages the probe includes interface means for the temperature sensing means and for the inflation of the catheters at the connection between the first and second stages of the probe.

If desired, the exposed antenna portion may include guidance means for selective transmission of the microwaves. The guidance means may comprise a thin metallic layer tapering toward the outer end of the exposed antenna portion to equalise leakage of the microwave energy along the length of the exposed portion. The metal may be Chromium which varies in thickness along the length of the rod instigating a differential relationship of wave reflection and transmission, thus radiating power evenly across the cylindrical area of the probe. Alternatively the guidance means could be mesh varying in grading along the exposed length of the rod or spaced sold rings the spacing between which is gradually increased.

Where the probe is to be used for medical treatment such as endometrial ablation it is important that the probe be sterile for each use. Although it would be possible to provide a disposable probe this is regarded as unnecessarily expensive. Accordingly, preferably the probe includes a removable and disposable sheath which encapsulates the probe during use.

Therefore, according to another aspect of the invention there is provided a protection means for a probe for applying electromagnetic radiation at microwave frequency to a body, said protection means comprising a sheath having a tubular body which may pass over the probe to encapsulate the operative end of the probe and which is substantiality transparent to microwaves at the intended frequency of operation, and means for securing the sheath in position whereby the sheath may be removed and disbanded after use of the probe. Preferably the sheath is transparent and the waveguide includes a graticule or measurement marking to aid insertion.

The protection means preferably further Includes a disposable handle arranged to receive a probe in use, the handle being locked in position about the probe by interengagement with the sheath. The protection means suitably includes a unique marking, such as a bar code, to ensure single use. the protective sheath may also include a bar code.

Although the probe and apparatus of the present invention may be used for any desired application it is preferred that the probe be used for endometrial ablation. Therefore, according to the preferred method of the invention there is provided a method of endometrial ablation comprising the steps of providing a probe as aforesaid having at least an operative end of outside dimensions no greater khan the dimensions of a dilated cervix, inserting the operative end of the probe through the cervix into the uterus, applying microwave energy to the probe at a frequency which will be substantially completely absorbed by the endometrium, monitoring the operating temperature to ensure that the endometrium tissue is heated to about 60° C. and maintaining the application of the microwave energy for a period of time sufficient to destroy the cells of the endometrium. The microwave energy may be applied continually or in pulses.

The use of microwave power to heat the endometrium has two main advantages. Firstly, electromagnetic radiation at microwave frequencies is strongly absorbed by tissue and at around 8–12 GHz all microwave power is absorbed in a layer of tissue about 5 mm thick and it is impossible for microwave heating to extend beyond this region. This is ideal for the treatment of the endometrium which is about 5 mm thick. Secondly, because of this strong absorption, the amount of power required to achieve the desired temperature is relatively small compared with RF frequencies and it is likely that the necessary energy could be delivered over a much shorter period than other current treatments take. If desired the radiation might be pulsed so that the tissue is momentarily heated above 60° C. and the total treatment time could then be shorter still.

The depth of material over which the microwave power is absorbed depends upon frequency and the material electrical properties. To set this to be around 5 mm in the endometrial tissue requires a frequency of about 8–12 GHz. This frequency then determines the dimensions of the waveguide needed to carry the wave. If a conventional waveguide were used a diameter of around 20 mm would be required. This is clearly far too large to enter the uterus. In accordance with the Invention cut-off wavelength is effectively reduced by the use of high dielectric constant material such as ceramic material or plastics dielectric material or other suitable material which provides a transition to a waveguide of outside diameter of about 8 mm.

With the probe of the present invention there is no possibility of radiation leakage and inadvertent heating occurring outside of the uterus along the Line delivering power to the implanted antenna. The problem of delivering power through the narrow neck has therefore been solved.

Having delivered the power into the uterus, the power is then distributed uniformly into the roughly flat triangular shaped pouch formed by the uterus by means of the exposed portion of the antenna which is arranged to prevent radiation escaping close to the input end. The temperature increase necessary to destroy the cells of the endometrium may require only 60 watts of microwave power to provide a treatment time of 2.5 minutes.

It may be found that access to the inner wall of the uterus is difficult and in such a case, there is an attribute of microwaves which can be used to advantage to provide an even distribution of the heating effect. In particular, microwaves will only be strongly absorbed by tissue and not by any intervening gas. If desired the uterus may be inflated by a gas such as carbon dioxide so that the walls will be held away from the antenna and receive an even radiation dose. The gas may be supplied through a central bore formed in the ceramic rod/ If the probe includes inflatable catheters then these may be selectively inflated as required to aid insertion and positioning within the uterus. The probe may also be provided with fibre-optic vision if desired.

The invention also includes a system for selective microwave transmission comprising a probe as aforesaid and a source of microwave energy. Preferably, the variable parameters of the system are computer controlled.

BRIEF DESCRIPTION OF THE DRAWINGS

The invention will now be described by way of example with reference to the accompanying drawings in which:

FIG. 1 is a diagrammatic side elevation of a preferred probe in accordance with the invention;

FIG. 3 is a diagrammatic side elevation of a second embodiment of probe in accordance with the invention;

FIG. 5 is a diagrammatic side elevation of a third embodiment of probe in accordance with the invention;

FIG. 6 is a diagrammatic side elevation of a fourth embodiment of probe in accordance with the invention;

FIG. 7 is a diagrammatic side elevation of a probe in accordance with the invention including a protective sheath;

DESCRIPTION OF THE PREFERRED EMBODIMENTS

Figure 2:
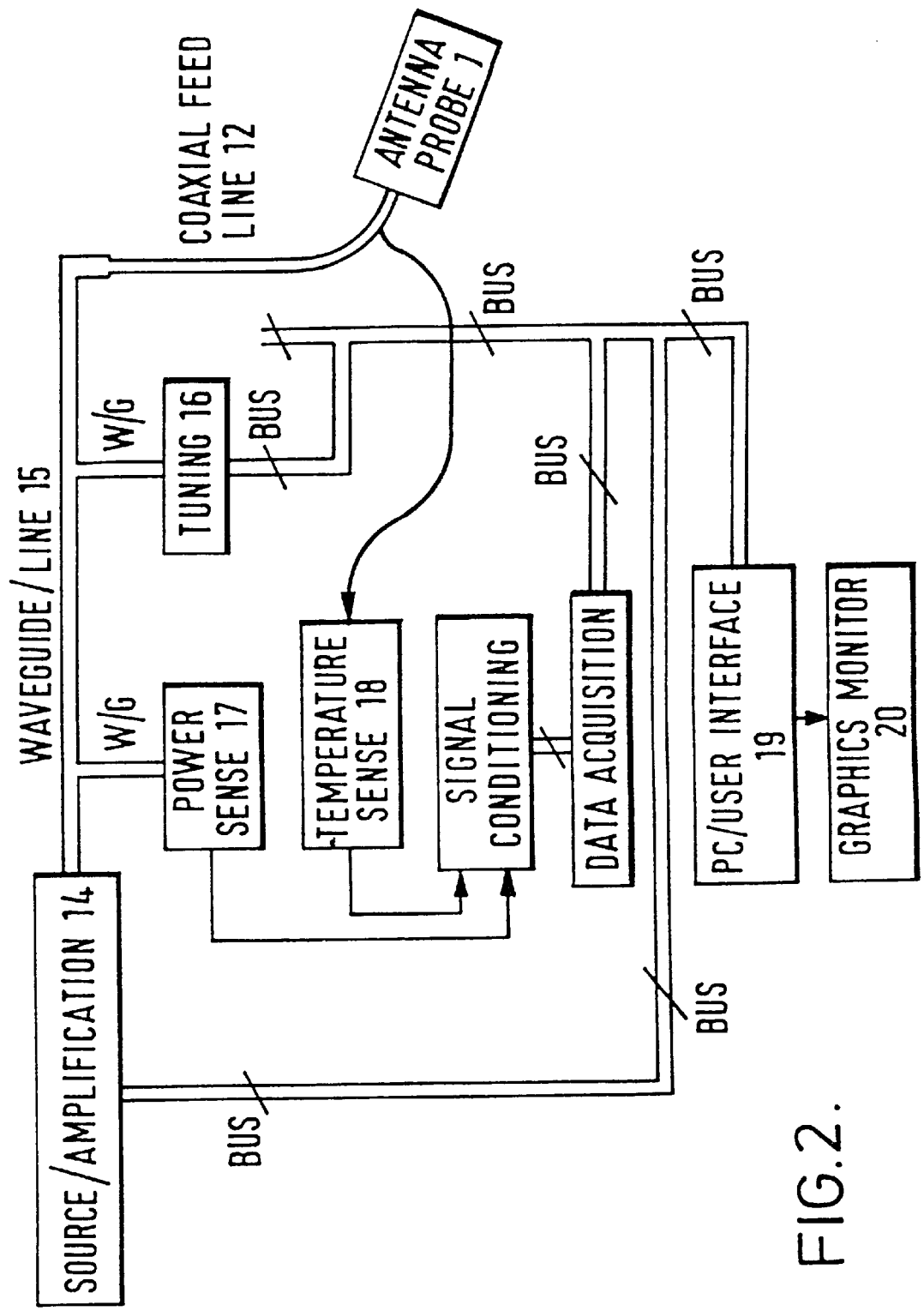
FIG. 2 is a block diagram of the preferred system incorporating the probe of FIG. 1.

In FIG. 1 a microwave probe (1) has a first circular waveguide (2) of a first diameter at one end being of custom-determined diameter according to probe use and a second circular waveguide (3) of a second, larger diameter at the other end. The transition between the first waveguide (2) and the larger diameter second waveguide (3) comprises a frusto-conical waveguide (4) and a dielectric rod (5) located mainly within the first waveguide (2). The dielectric rod (5) has a tapered end (6) extending into the transition waveguide (4). Disposed about the dielectric tapered end (6) is a dielectric buffer plug (7) having dielectric properties greater than air but less than that of the dielectric rod (6).

The first waveguide (2) extends towards the free end of the probe (1) but terminates short of the free end to leave an exposed antenna portion (8). The exposed antenna portion (8) and the first waveguide (2) are provided with a protective removable and disposed sheath (9) of bio-medically inert and microwave transparent material, for example a protective PTFE or similar material, which may be profiled as shown according to probe use. In order to sense the operating temperature, the probe (1) includes thermocouple wire temperature sensing means (10).

As can be seen from FIG. 1 the second waveguide (3) also includes waveguide tuning stubs (11). The stubs (11) are set in the wall of the second waveguide (3) to provide means of intrinsically matching the antenna portion (8) in a body. A probe matched to a specific load, preferably endometrium tissue in this application will relieve the need for extensive pre-operative tuning. In addition, the provision of stubs (11) limit the existence of standing waves in the coaxial feed line (12) which can form there when matching is initiated at the system tuning network end of the coaxial feed line. Standing waves in the coaxial feed line will generate heat and reduce the working life of the cable.

However, subtle load variations from patient to patient can be fine tuned using the system tuning network (13) shown in FIG. 2. In FIG. 2, the probe (1) of the invention is supplied with a microwave frequency input in the microwave spectrum, preferably in the region of 8–12 GHz, from a microwave frequency generator source and amplifier (14). The amplified signal is passed to the probe (1) via waveguide line (15) and the coaxial feed line (12). Although, the provision of stubs (11) permits the tuning of the probe to the specific load, fine tuning is provided by the tuning network (16) controls the fine turning of the match of power into the loaded probe. The power level of the source/amplification unit (14) is monitored by a power sense (17) on the waveguide line (15). A thermometry unit (18) is provided to take temperature sensor readings at the probe/tissue interface (1). The various signals are collated and conditioned and fed to a PC/user interface (19) which may interface with a user's conventional PC graphics monitor (20). In this way the user may vary the frequency of the source (14), set the power level required, and vary the tuning network (16) to achieve optimum match into a load. Also during the treatment, real-time graphs of temperature data can be viewed on the monitor (20).

Figure 4:
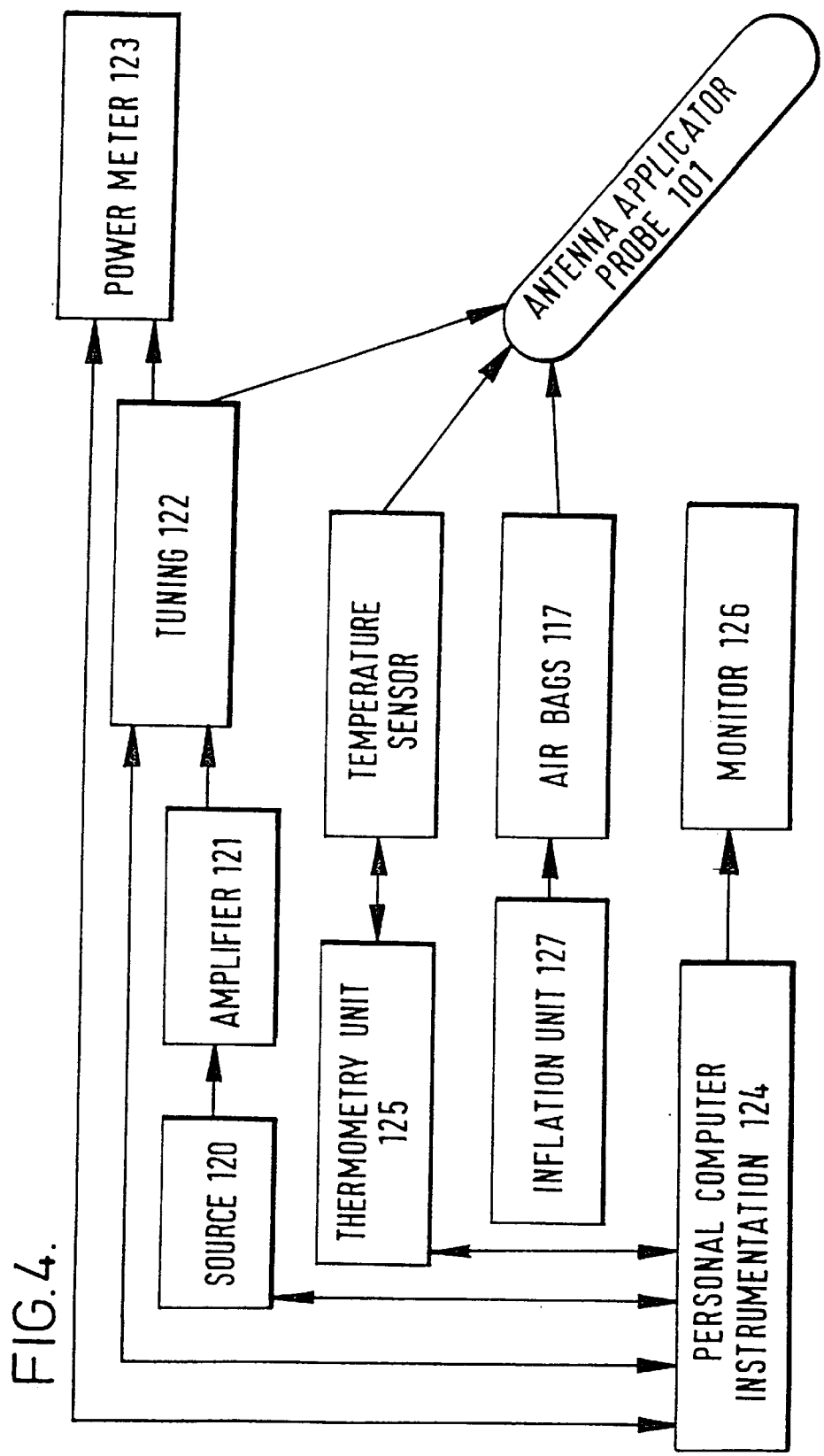
FIG. 4 is a block diagram of the system incorporating the probe of FIG. 3.

In the embodiment of FIGS. 3 and 4 the probe arrangement is similar to that described with reference to FIGS. 1 and 2 except that the probe is formed in two parts. In FIG. 3 a microwave probe (101) has a dielectric input stage (102) and a dielectric output stage (103). The input stage (102) includes a circular waveguide (104) of a first diameter at one end and a circular waveguide (105) of a second, smaller diameter at the other end, the diameter being of custom-determined diameter according to probe use. The transition between the waveguide (104) and the smaller diameter waveguide (105) comprises a frusto-conical waveguide (106) and a first dielectric rod (107) located mainly within the waveguide (105) but having a tapered end (108) extending into the transition waveguide (106). Disposed about the dielectric tapered end (108) is a dielectric buffer plug (109) having dielectric properties greater than air but less than that of the dielectric rod (107). The circular waveguide (105) terminates in a flange (110) and the rod (107, extends beyond the flange (110) to a joint (111).

The dielectric output stage (103) includes a second dielectric rod (112), an inner end of which abuts the end of the dielectric rod (107 at the joint (111). The output stage (103) is provided with a further waveguide (113) which extends from the flange (110) towards the free end of the probe (101). However, the waveguide (113) terminates short of the free end of the probe (101) to leave an exposed antenna portion (114). The exposed antenna portion (114) and the waveguide (113) are provided with a protective sheath (115) of PTFE or other suitable material as with the first embodiment. In order to sense the operating temperature, the probe (101) includes thermocouple wire temperature sensing means (130). The temperature sensing means (130) is connected to a temperature sensor interface (116) at the flange (110).

The probe (101) disclosed by way of example is a probe for endometrial ablation and, in order to facilitate insertion of the probe inside the uterus, the probe (101) includes two balloon catheters (117) (only one shown), one fixed to each side of the waveguide (113). The catheters (117) are provided with air by means of air tubes (118) and an air tube interface (119) is provided adjacent the flange (110) on the circular waveguide (105).

The probe system of FIG. 3 is preferably arranged as disclosed in FIG. 4. In that arrangement, it will be seen that the probe (101) is supplied with a microwave frequency input in the region of 8–12 GHz from a microwave frequency generator source (120), the signal of which is amplified by amplifier (121) and passed through a tuning network (122) before entering the input dielectric stage (112) at the circular waveguide (114). The tuning network (122) controls the match of power into a loaded probe (101) and the match is monitored using a power meter (123). Personal computer instrumentation (124) is used to vary the frequency of the source (120), set the power level required, and vary the tuning network (122) to achieve optimum match into a load. This could also be done manually, if required. A thermometry unit (125) is provided to take temperature sensor readings from the probe (101) received via the interface (116) and store these on disk in the p.c. (124). During the treatment, real-time graphs of temperature data can be viewed on the monitor (126).

In order to facilitate manipulation of the probe within the uterus, an inflation unit 127 is provided which is operative to supply sufficient air pressure to inflate the catheters (117) on the probe surface.

The probe 140 of the embodiment of FIG. 5 as similar to that of FIG. 3 and where appropriate similar references have been used. The main difference in the embodiment of figure is that the waveguide surrounding the dielectric rod (107) is formed by thermocouple wire 142 coil ed about the exposed antenna portion 114 for temperature sensing. The flange 110 is again separable into two parts 144,146 each of which includes thermocouple connectors allowing connection of the thermocouple wire 142 to a thermocouple interface 148. In order to serve as a waveguide as well the thermocouple wire 142 is wound so as to provide controlled radiation along the length of the dielectric rod 107.

The embodiment of FIG. 6 is an alternative arrangement where there is a single wave guide. In this arrangement a microwave probe 201 has a circular waveguide 202 filled with a dielectric material 23. The waveguide 202 terminates short of the end of the probe 201 providing an exposed antenna portion Ant. Towards the end of the probe 201 remote from the exposed antenna portion 204 there is a coaxial feed line input 205 and a waveguide excitation stud 206. which directly excites the dielectric filled waveguide 202. The probe 201 is matched to the load of the body Into which it is to be inserted by means of tuning stubs 207 fixed to the wall of the waveguide 202.

As with previous embodiment, the probe 201 is provided with a protective sheath 208 of PTFF or other suitable material and reference is particularly directly to the disclosure of one form of the sheath given in FIG. 7. A temperature sensor 209 is provided between the sheath 208 and the waveguide 202 feeding a temperature indicative signal back to the control (not shown).

In FIG. 7 an embodiment similar to the embodiments of FIG. 3–5 is illustrated where the probe 301 Includes a first waveguide 302 of small diameter, a second waveguide 303 of Larger diameter and a frusto-conical transition waveguide 304 between the two. The first waveguide includes a dielectric rod 305 one end 306 of which is tapered at the transition and the other end of which provides an exposed antenna portion 307. The respective waveguides are interconnected by flange fittings 308,309. The first waveguide 302 is protected by a sheath 310 of bio-medically inert material which is substantially transparent to microwave energy of the desired frequency. The sheath 310 is arrange to interconnect with the flange 309 so as to be removable and replaceable after each use of the probe. The second waveguide 303 includes an excitation stub 311 which receives input from coaxial cable 312. The interconnection between the sheath 310 and the flange 309 is shown diagrammatically but will comprise a sacrificial joint causing breakage of the sheath 310 on removal, eg. it may comprise co-operating wedged ribs on the sheath 310 and the flange 309 which allow engagement but resist disengagement without breakage.

Figure 8A:
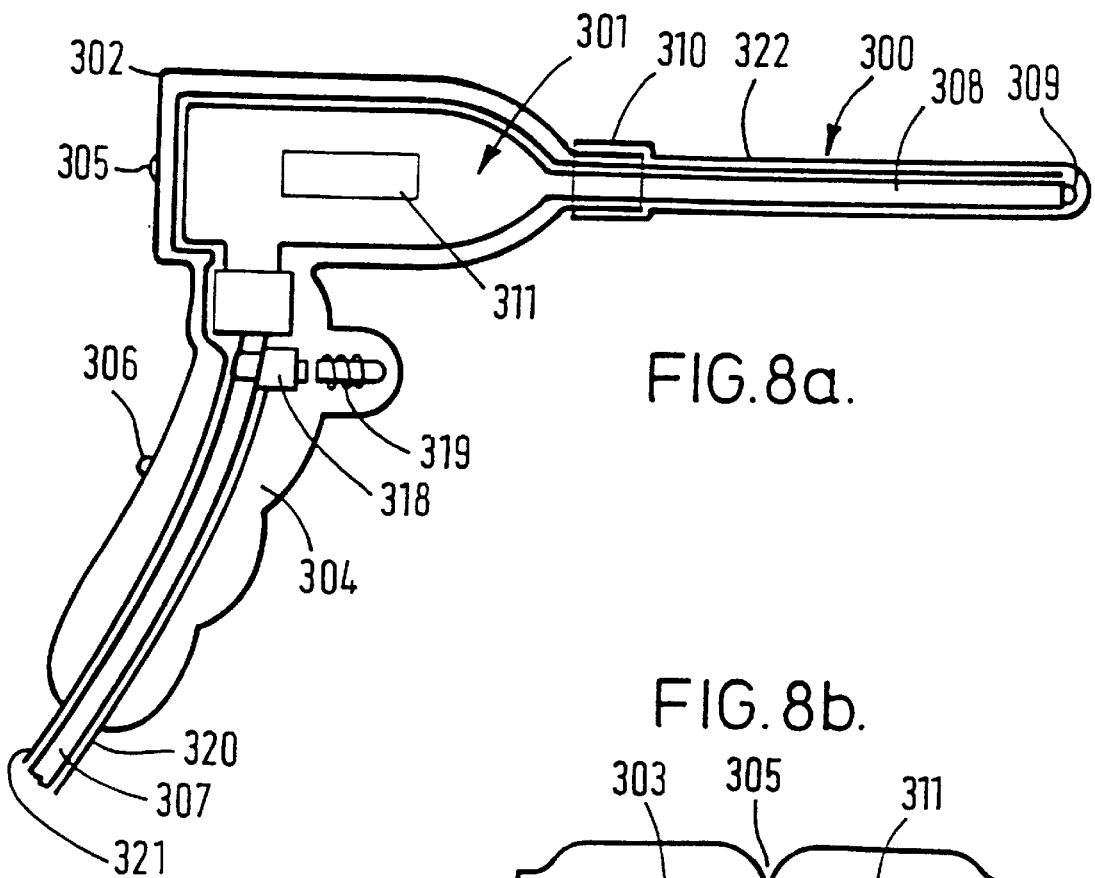
FIGS. 8a, 8b and 8c are diagrammatic views of an arrangement for ensuring single use of the protective sheath.
Figure 8B:
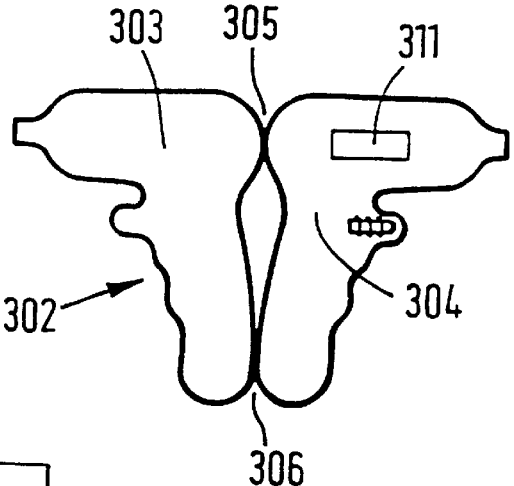
Figure 8C:
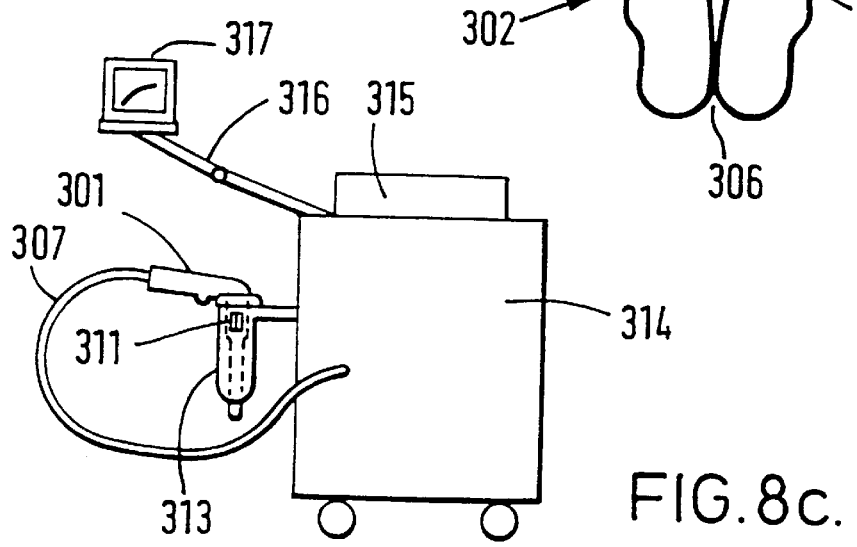

The arrangement of FIGS. 8a, 8b and 8c employs a protective sheath 320 and a disposable handle 302 which can be supplied in a sterile pack for single use only. In order to ensure disposal of the protective sheath 300, and the handle 302 following use, the probe 301, of construction as exemplified in FIG. 1, is housed in the handle 302 for use. The handle 302 comprises two halves 303, 304 hinged at hinge points 305, 306. the handle 302 is moulded of microwave absorbing material and the hinged halves 303, 304 fold around the probe base and cable 307 leaving the first dielectric filled waveguide 308 and antenna portion 309 protruding from the handle as shown.

The two halves 303, 304 of the handle 302 are secured together by means of the protective sheath and antenna portion 309. The sheath 300 has a sacrificial join 310 which fits over the handle halves 303, 304 and can only be removed by breaking the join 310. The sheath 300 is moulded from a biomedical material that is low-loss to microwaves.

In order to control use of the disposable handle 302 and reference the disposable items to a systems treatment log, a bar code 311 is used which can be automatically read by a bar code reader (not shown) when the assembled probe is placed in a system holster 313. The holster 313 is provided on a trolley 314 including the control elements of the system described in more detail with reference to FIG. 2. For example, a control keypad 315, display arm 316 and display 317 are shown.

In order to ensure that a handle 302 and sheath 300 are used with the probe 901, the cable 307 suitably Includes a control switch 318 which is operative by means of a spring switch 319 on the handle 302. The control switch 318 is operative through were 320 in the cable 307 which also includes a wire 321 from the thermocouple temperature sensor 322. The bar code 311 on the handle 302 will be unique and the software of the system is designed to reject second use to ensure disposal and replacement by a new sterile pack comprising handle and sheath for each treatment. If desired, the sheath may also include a bar code and the bar code may include batch and date information for data logging purposes.

In most applications, and particularly, in the preferred method of the invention, the probe will be used to apply heat to a load. When the load is of a biological nature, the addition of temperature sensors in the probe body as shown in some of the figures is important for safety, monitors allowing for in-situ temperature readings which can be input to feedback control and data logging systems.

Figure 9A:
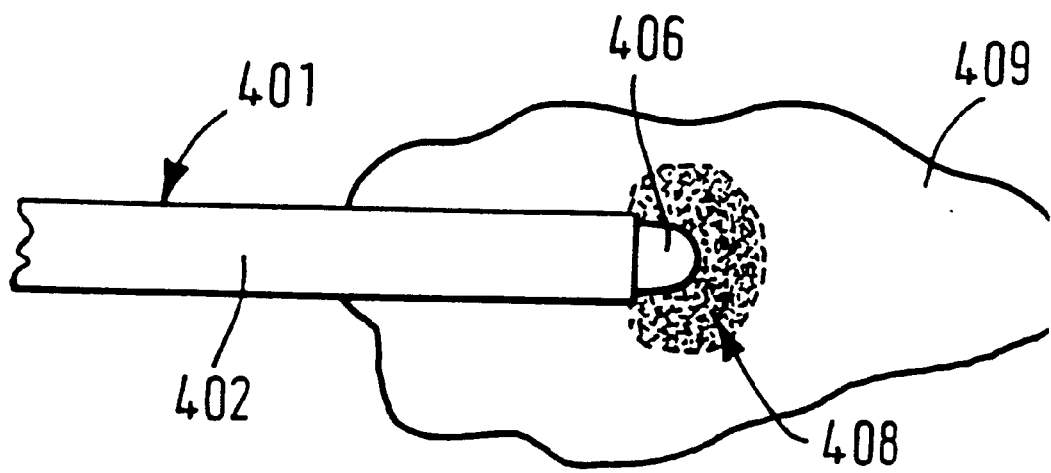
FIGS. 9a and 9b are simplified views showing a probe of the present invention in use.
Figure 9B:
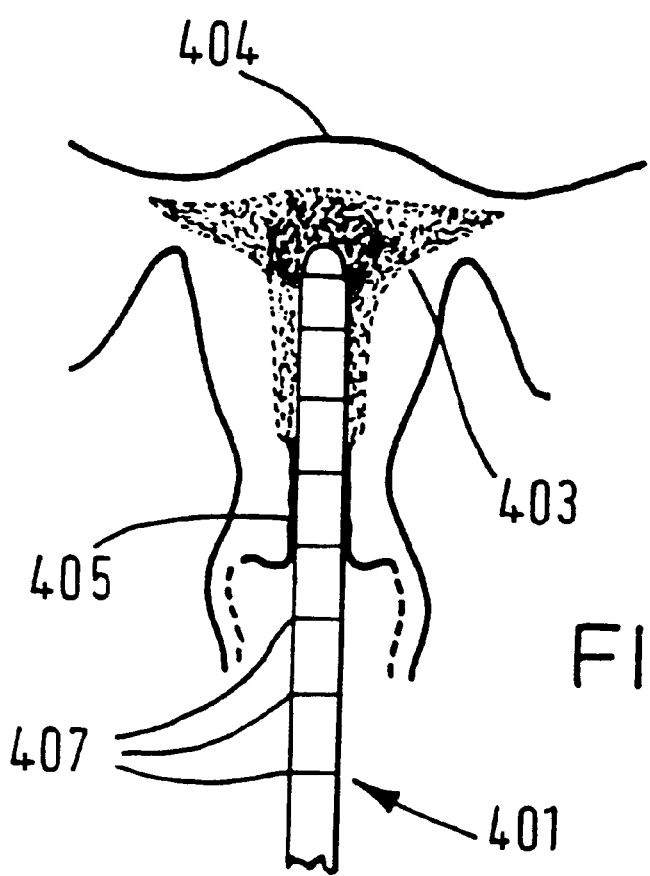

In use, with reference to diagrammatic FIGS. 9a and 9b, the probe 401 of the invention is supplied with a microwave frequency or put in the region of 8–12 GHz from microwave frequency generator. The dielectric material 402 within the first waveguide optimists a smooth transition without causing undue reflection. The probe 401 is suitably provided with a handle allowing manipulation by the operator and providing sterile single use as described by way of example with reference to FIGS. 8a, 8b, 8c.

The patient is prepared by drugs being administered to contract the endometrial layer 403 of the uterus 404 as necessary. The cervix 405 is dilated and the surgeon, will then insert a tool (not shown) to determine the depth of the uterus 404 to determine the area for treatment. The probe 401 is then inserted into the uterus 404 and the probe tip 406 positioned using markers 407 on the length of the probe as shown diagrammatically.

When the applicator tip is placed in biological tissue the generated field shape 408 in the tissue 409 can be a uniform sphere-like shape of about 4–5 mm from the dielectric surface of the probe tip 406 as shown diagrammatically in FIG. 9a.

Electromagnetic heating of the tissue 409 only occurs within this sphere.

In the particular treatment disclosed the probe 401 is inserted to the fundus of the uterus 404 and the probe 401 slowly withdrawn to expose the full endometrial lining to the electromagnetic field. The microwave electromagnetic energy radiated from the exposed probe tip 406 heats the localised area of endometrium 43 and during treatment the temperature is continually monitored by means of the temperature sensors. Thus, for example, the power may be switched on for a period of 9 seconds and then switched off for a period of 1 second whilst the temperature is measured. Whilst the control in this respect may be manual it is preferred to provide an automatic control system for maintaining the controlling temperature by means of the fibre-optic thermometry systems and data acquisition and control means.

The microwave energy is strong absorbed by the tissue of the endometrium and, by controlling the frequency and the power, the depth of absorption can be restricted solely to the endometrium itself which is about 5 mm in depth. This has the advantage that physical injury or radiation effects on surrounding tissue are avoided. The markers 407 on the probe 401 assist the surgeon in knowing where the probe tip 406 is in the uterine cavity during treatment.

The treatment time is likely to be less than 20 minutes minimising gynaecclogist time and allowing the patient a minimum time in hospital typically 1 day or less. The treated endometrium is left as scar tissue.

Although, the invention has been described using substantially continuous heating using lower power eg 60 watts to achieve a temperature in excess of 60° C., the microwave electromagnetic energy may be pulsed at a much higher power by means of a pulse magnetron. This provides pules of kilowatt power in microseconds each pulse being spaced by the order of a millisecond. For example, it may be possible to provide pulses with a peak output of 80 kilowatts for a duration of 1 microsecond spaced by 1 millisecond. Pulsing may have the advantage of countering the body's natural reaction to continuous heating of tissue of increasing the blood flow to the area being treated to provide cooling. Thus continuous heating may not be as efficient in destroying the cells as pulsed heating where the effect of the increased blood flow is minimised or not even promoted in the first instance.

From the drawings it will be seen that the probe of the present invention is designed to propagate and radiate microwave electromagnetic energy in a controlled fashion. The design makes use of a dielectric material within a circular waveguide with dimensions dictated by the microwave frequency used and the electrical properties of the dielectric material. The preferred dielectric material is alumina which provides an antenna diameter which is compatible with the narrow neck the uterus. However, choosing a material with a higher dielectric constant, this diameter could be made even smaller. The dielectric material may be ceramic, plastics or other suitable material.

Although, the choice of dielectric material will fix the probe diameter, the tip of the exposed antenna portion will be shaped to achieve the desired radiation pattern. The profile of the protective sheath can also be shaped to provide more accurate coverage of radiation in a specifically shaped load. In certain applications part of all of the probe may be designed to swivel or rotate to achieve better radiation coverage across a load. Thus, careful design of the shape and size of the probe will automatically match it to an application specific load, thus reducing the effects of standing waves which can cause loss of power and hot spots. This optimum matching can be offset by the variance of load shape and size. Tuning can be done by introducing tuning screws into the antenna/waveguide body or by adding specifically designed metal tuning washers into the dielectric/antenna assembly.

The protective sheath is, preferably of a sterile, single use, and disposable design will be used to provide a medically inert external for all parts of the probe that come in contact with a body. The material will be medically inert, low-loss at microwave frenzies, capable of withstanding extended exposure to harsh chemicals and high temperatures, and it will lend itself to production molding techniques. The protective sheath suitably includes a bar code to ensure single use to prevent cross-contamination and to provide traceability.

As an alternative to bar codes, the unique identification means may comprise any other suitable means, eg. a passive electronic transporter which, if desired, may be embedded in the material of the protective sheath and/or the handle.

We claim:

1. A probe for applying electromagnetic radiation at microwave frequency to a body region accessible through an opening of the body, comprising:

an input for receiving microwave signal input of a predetermined frequency;

a first waveguide for receiving and propagating said microwave frequency input, said waveguide having an external diameter that fits within the opening and being of a cross-sectional dimension which would not normally pass the microwaves at said frequency;

dielectric material within the first waveguide, the dielectric constant of which varies the cut-off frequency of the waveguide so that the waveguide can propagate desired modes of the microwaves; and a portion of dielectric material protruding from the waveguide at the active end of the probe and forming an antenna which is shaped to control wave transmission away from the probe;

whereby the first waveguide is insertable through the opening to place the antenna in operative relation with a body region.

2. A probe according to claim 1, wherein the tip of the exposed antenna portion is shaped to achieve a desired radiation pattern.

3. A probe according to claim 1, wherein the first waveguide is a waveguide of circular cross-section.

4. A probe according to claim 1 wherein the input for receiving the microwave signal comprises a second waveguide, air filled with a larger cross-sectional dimension than the first waveguide and a tapered waveguide section interconnecting the first waveguide with the second waveguide so as to provide transmission of the microwaves with minimal reflection at the interface between the first and second waveguides.

5. A probe according to claim 4, wherein the dielectric material tapers within the tapered waveguide section to optimize transmission of the microwaves with the minimal reflection.

6. A probe according to claim 4, wherein the second waveguide includes tuning stubs providing means adapted for matching the antenna to the load of the body into which the probe is to be inserted.

7. A probe according to claim 3, wherein there is a single waveguide and the input for receiving the microwave input directly excites the dielectric filled waveguide of the desired smaller cross-sectional dimension.

8. A probe according to claim 7, wherein the input for receiving the microwave input comprises a co-axial feed line input and a waveguide excitation stub which directly excites the dielectric filled waveguide.

9. A probe according to claim 7, wherein the probe is adapted to be matched to the load of the body into which it is to be inserted by means of tuning stubs secured to a wall of the waveguide.

10. A probe according to claim 1, including temperature sensing means.

11. A probe according to claim 10, wherein the temperature sensing means is disposed between the first waveguide and a protective sheath.

12. A probe according to claim 1, includes a protective sheath which encapsulates the probe during use.

13. A probe according to claim 12, wherein the protective sheath provides a medically inert external coating for all parts of the probe that come into contact with a body.

14. A probe according to claim 12, wherein the protective sheath is a sterile, single-use and disposable sheath and which comprises a tubular body which is substantially transparent to microwaves at an intended frequency of the operation, which, in use, may be passed over the probe to encapsulate the operative end of the probe; and means whereby the sheath may be secured in position during use of the probe and may be removed and discarded after use of the probe.

15. A probe for applying electromagnetic radiation at microwave frequency to a body region accessible through an opening of the body, comprising:

means for receiving microwave signal input of a predetermined frequency;

a first waveguide for receiving and propagating said microwave frequency input, said waveguide having an external diameter that fits within the opening and being of a cross-sectional dimension which would not normally pass the microwaves at said frequency;

dielectric material within the first waveguide, the dielectric constant of which varies the cut-off frequency of the waveguide so that the waveguide can propagate desired modes of the microwaves;

a portion of dielectric material at or adjacent to the active end of the probe forming an antenna which controls wave transmission away from the probe, whereby the first waveguide is insertable through the opening to place the antenna in operative relation with a body region;

the means for receiving the microwave signal comprising a second waveguide, air filled with a larger cross-sectional dimension than the first waveguide and a tapered waveguide section interconnecting the first waveguide with the second waveguide so as to provide transmission of the microwaves with minimal reflection at the interface between the first and second waveguides;

the dielectric material tapering within the tapered waveguide section to optimize transmissions of the microwaves with the minimal reflection; and a dielectric buffer inside the tapered waveguide section, the dielectric constant of which is greater than air and less than that of the dielectric taper.

16. A probe for applying electromagnetic radiation at microwave frequency to a body region accessible through an opening of the body, comprising:

means for receiving microwave signal input of a predetermined frequency;

a first waveguide for receiving and propagating said microwave frequency input, said waveguide having an external diameter that fits within the opening and being of a cross-sectional dimension which would not normally pass the microwaves at said frequency;

dielectric material within the first waveguide, the dielectric constant of which varies the cut-off frequency of the waveguide so that the waveguide can propagate desired modes of the microwaves;

a portion of dielectric material at or adjacent to the active end of the probe forming an antenna which controls wave transmission away from the probe, whereby the first waveguide is insertable through the opening to place the antenna in operative relation with a body region; and temperature sensing means disposed between the first waveguide and a protective sheath, and comprising sensors disposed at different locations along the length of the probe to detect the temperatures at said different locations.

* * * * *